United States Patent
Krivanek

(10) Patent No.: US 12,137,663 B2
(45) Date of Patent: Nov. 12, 2024

(54) TOMATO HYBRID SVTH2909 AND PARENTS THEREOF

(71) Applicant: Seminis Vegetable Seeds, Inc., St. Louis, MO (US)

(72) Inventor: Alan Krivanek, Woodland, CA (US)

(73) Assignee: SEMINIS VEGETABLE SEEDS, INC., St. Louis, MO (US)

( * ) Notice: Subject to any disclaimer, the term of this patent is extended or adjusted under 35 U.S.C. 154(b) by 269 days.

(21) Appl. No.: 17/812,090

(22) Filed: Jul. 12, 2022

(65) Prior Publication Data

US 2024/0016112 A1 Jan. 18, 2024

(51) Int. Cl.
*A01H 6/82* (2018.01)
*A01H 5/08* (2018.01)

(52) U.S. Cl.
CPC .............. *A01H 6/825* (2018.05); *A01H 5/08* (2013.01)

(58) Field of Classification Search
None
See application file for complete search history.

(56) References Cited

U.S. PATENT DOCUMENTS

| | | | | |
|---|---|---|---|---|
| 10,219,458 | B2 * | 3/2019 | Petersen | A01H 6/825 |
| 11,076,571 | B1 | 8/2021 | Krivanek | |
| 11,191,247 | B1 | 12/2021 | Krivanek | |
| 2009/0188007 | A1 | 7/2009 | Maris et al. | |
| 2010/0146659 | A1 | 6/2010 | Heuvel et al. | |
| 2016/0128293 | A1 | 5/2016 | Brugmans et al. | |
| 2019/0211351 | A1 | 7/2019 | Graham et al. | |
| 2020/0048655 | A1 | 2/2020 | Allersma et al. | |
| 2021/0329876 | A1 | 10/2021 | Krivanek | |
| 2024/0224922 | A1 | 7/2024 | Krivanek | |

OTHER PUBLICATIONS

Larkin et al., "Somaclonal variation—a novel source of variability from cell cultures for plant improvement," *Theor Appl Genet*, 60(4):197-214; 1981.
Moose et al., "Molecular plant breeding as the foundation for 21st century crop improvement," *Plant Physiol*, 147(3):969-77, 2008.
Variety specific information as indicated in transmittal letter of the Information Disclosure Statement for U.S. Appl. No. 17/812,090, filed Dec. 7, 2022.
Variety specific information as indicated in transmittal letter of the Information Disclosure Statement for U.S. Appl. No. 16/783,770, filed Apr. 22, 2020.
Community Plant Variety Office, Application for Community Plant Variety Right to the Community Plant Variety Office, with Technical Questionnaire, Breeder's ref.: FIR-180-ZONA, published Oct. 15, 2019.
Variety specific information as indicated in the transmittal letter of the Information Disclosure U.S. Appl. No. 18/094,193, filed Jun. 30, 2023.

* cited by examiner

*Primary Examiner* — Medina A Ibrahim
(74) *Attorney, Agent, or Firm* — Dentons US LLP; Alissa Eagle

(57) ABSTRACT

The invention provides seeds and plants of tomato hybrid SVTH2909 and tomato line FIR-A818-0160. The invention thus relates to the plants, seeds, plant parts, and tissue cultures of tomato hybrid SVTH2909 and tomato line FIR-A818-0160 and to methods for producing a tomato plant produced by crossing such plants with themselves or with another plant, such as a tomato plant of another genotype. The invention further relates to seeds and plants produced by such crossing. The invention further relates to plants, seeds, plant parts, and tissue cultures of tomato hybrid SVTH2909 and tomato line FIR-A818-0160 comprising introduced beneficial or desirable traits.

24 Claims, No Drawings

TOMATO HYBRID SVTH2909 AND PARENTS THEREOF

FIELD OF THE INVENTION

The present invention relates to the field of plant breeding and, more specifically, to the development of tomato hybrid SVTH2909 and tomato line FIR-A818-0160.

BACKGROUND OF THE INVENTION

The goal of vegetable breeding is to combine various desirable traits in a single variety. Such desirable traits may include any trait deemed beneficial or desirable by a grower or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all genetic loci and produce a uniform population of true breeding progeny, a homozygous plant. A cross between two such homozygous plants of different genotypes produces a uniform population of hybrid plants that are heterozygous for many genetic loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a tomato plant of hybrid SVTH2909 or line FIR-A818-0160. Also provided are tomato plants having all the physiological and morphological characteristics of such a plant. Parts of these tomato plants are also provided, for example, including pollen, an ovule, an embryo, a seed, a scion, a rootstock, a fruit, and a cell of the plant.

In another aspect of the invention, a plant of tomato hybrid SVTH2909 or tomato line FIR-A818-0160 comprising an added heritable trait is provided. The heritable trait may comprise a genetic locus that is, for example, a dominant or recessive allele. In one embodiment of the invention, a plant of tomato hybrid SVTH2909 or tomato line FIR-A818-0160 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan.

The invention also concerns the seed of tomato hybrid SVTH2909 or tomato line FIR-A818-0160. The seed of the invention may be provided as an essentially homogeneous population of seed of tomato hybrid SVTH2909 or tomato line FIR-A818-0160. Essentially homogeneous populations of seed are generally free from substantial numbers of other seed. Therefore, seed of tomato hybrid SVTH2909 or tomato line FIR-A818-0160 may be defined as forming at least about 97% of the total seed, including at least about 98%, 99%, or more of the seed. The seed population may be separately grown to provide an essentially homogeneous population of tomato plants designated SVTH2909 or FIR-A818-0160.

In yet another aspect of the invention, a tissue culture of regenerable cells of a tomato plant of hybrid SVTH2909 or tomato line FIR-A818-0160 is provided. The tissue culture will preferably be capable of regenerating tomato plants capable of expressing all of the physiological and morphological characteristics of the starting plant and of regenerating plants having substantially the same genotype as the starting plant. Examples of some of the physiological and morphological characteristics of tomato hybrid SVTH2909 or tomato line FIR-A818-0160 include those traits set forth in the tables herein. The regenerable cells in such tissue cultures may be derived, for example, from embryos, meristems, cotyledons, pollen, leaves, anthers, roots, root tips, pistils, flowers, seed, and stalks. Still further, the present invention provides tomato plants regenerated from a tissue culture of the invention, the plants having all the physiological and morphological characteristics of tomato hybrid SVTH2909 or tomato line FIR-A818-0160.

In still yet another aspect of the invention, processes are provided for producing tomato seeds, plants, and fruit, which processes generally comprise crossing a first parent tomato plant with a second parent tomato plant, wherein at least one of the first or second parent plants is a plant of tomato line FIR-A818-0160. These processes may be further exemplified as processes for preparing hybrid tomato seed or plants, wherein a first tomato plant is crossed with a second tomato plant of a different, distinct genotype to provide a hybrid that has, as one of its parents, a plant of tomato line FIR-A818-0160. In these processes, crossing will result in the production of seed. The seed production occurs regardless of whether the seed is collected or not.

In one embodiment of the invention, the first step in "crossing" comprises planting seeds of a first and second parent tomato plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent tomato plants into plants that bear flowers. A third step may comprise preventing self-pollination of the plants, such as by emasculating the flowers (i.e., killing or removing the pollen).

A fourth step for a hybrid cross may comprise cross-pollination between the first and second parent tomato plants. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plants is a plant of tomato hybrid SVTH2909 or tomato line FIR-A818-0160. In one embodiment of the invention, tomato seed and plants produced by the process are first generation ($F_1$) hybrid tomato seed and plants produced by crossing a plant in accordance with the invention with another, distinct plant. The present invention further contemplates plant parts of such an $F_1$ hybrid tomato plant, and methods of use thereof. Therefore, certain exemplary embodiments of the invention provide an $F_1$ hybrid tomato plant and seed thereof.

In still yet another aspect, the present invention provides a method of producing a plant derived from tomato hybrid SVTH2909 or tomato line FIR-A818-0160, the method comprising the steps of: (a) preparing a progeny plant derived from tomato hybrid SVTH2909 or tomato line FIR-A818-0160, wherein said preparing comprises crossing a plant of tomato hybrid SVTH2909 or tomato line FIR-A818-0160 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from tomato hybrid SVTH2909 or tomato line FIR-A818-0160. The plant derived from tomato hybrid SVTH2909 or tomato line FIR-A818-0160 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from tomato hybrid SVTH2909 or tomato line FIR-A818-0160 is obtained which possesses some of the desirable traits of the line/hybrid as well as potentially other selected traits.

In certain embodiments, the present invention provides a method of producing food or feed comprising: (a) obtaining a plant of tomato hybrid SVTH2909 or tomato line FIR-A818-0160, wherein the plant has been cultivated to maturity, and (b) collecting at least one tomato from the plant.

In still yet another aspect of the invention, the genetic complement of tomato hybrid SVTH2909 or tomato line FIR-A818-0160 is provided. The phrase "genetic complement" is used to refer to the aggregate of nucleotide sequences, the expression of which sequences defines the phenotype of, in the present case, a tomato plant, or a cell or tissue of that plant. A genetic complement thus represents the genetic makeup of a cell, tissue or plant, and a hybrid genetic complement represents the genetic make-up of a hybrid cell, tissue or plant. The invention thus provides tomato plant cells that have a genetic complement in accordance with the tomato plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that tomato hybrid SVTH2909 or tomato line FIR-A818-0160 could be identified by any of the many well-known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps. Similarly, any plant that "comprises," "has," or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds, and derivatives of tomato hybrid SVTH2909, tomato line FIR-A818-0160, and tomato line FDR-A818-0310.

Tomato hybrid SVTH2909, also known as 16-A8-FIR-2909 and 16-A8-FIR-3576, is an indeterminate tomato variety that produces large, round excellent quality fruit with high yield. The hybrid is intended for net house and greenhouse environments. Tomato hybrid SVTH2909 comprises high resistance to ToMV:0-2/ToTV/Aal/Fol:0-2/For/Sbl/Sl/Ss/Va:0/Vd:0 and intermediate resistance to TSWV:0/TYLCV. The hybrid also comprises a ToMarV resistance trait described in U.S. Pat. Pub. No. 2010/0146659, a ToTV resistance trait described in U.S. Pat. Pub. No. 2009/0188007, a *Fusarium oxysporum* f. sp. *lycopersici* resistance trait described in U.S. Pat. Pub. No. 2019/0211351, a *Stemphylium* resistance trait described in U.S. Pat. Pub. No. 2020/0048655, and a TYLCV resistance trait described in U.S. Pat. Pub. No. 2016/0128293.

A. Origin and Breeding History of Tomato Hybrid SVTH2909

The parents of tomato hybrid SVTH2909 are tomato line FIR-A818-0160 and tomato line FDR-A818-0310. The parent lines are uniform and stable, as is a hybrid produced therefrom. A small percentage of variants can occur within commercially acceptable limits for almost any characteristic during the course of repeated multiplication. However no variants are expected.

B. Physiological and Morphological Characteristics of Tomato Hybrid SVTH2909 and Tomato Line FIR-A818-0160

In accordance with one aspect of the present invention, there are provided plants having the physiological and morphological characteristics of tomato hybrid SVTH2909 and the parent lines thereof. Descriptions of the physiological and morphological characteristics of such plants are presented in the tables that follow.

TABLE 1

Physiological and Morphological Characteristics of Tomato Hybrid SVTH2909

| CHARACTERISTIC | SVTH2909 | PINNACLE |
|---|---|---|
| Seedling | | |
| anthocyanin in hypocotyl of 2-15 cm seedling | present | present |
| habit of 3-4 week old seedling | normal | normal |
| Mature Plant | | |
| height (cm) | 155.64 | 150.00 |
| height | long | long |
| growth type | indeterminate | indeterminate |
| form | normal | lax, open |
| canopy size (compared to others of similar type) | large | large |
| habit | sprawling | semi-erect |
| Stem | | |
| anthocyanin coloration of upper third | absent or very weak | weak |
| length of internode | medium | medium |
| branching | intermediate | intermediate |
| branching at cotyledon or first leafy node | present | present |
| number of nodes between first inflorescence | 4.00 | 3.71 |
| number of nodes between early (first to second, second to third) inflorescences | 2.2 | 2.3 |
| number of nodes between later developing inflorescences | 1.50 | 1.93 |
| pubescence on younger stems | densely hairy or wooly | moderately hairy |
| Leaf | | |
| type (mature leaf beneath the third inflorescence) | tomato | tomato |
| type of blade | bipinnate | bipinnate |
| margins of major leaflets (mature leaf beneath the third inflorescence) | shallowly toothed or scalloped | deeply toothed or cut, sps. |
| marginal rolling or wiltiness (mature leaf beneath the third inflorescence) | slight | absent |
| onset of leaflet rolling (mature leaf beneath the third inflorescence) | late season | mid season |
| surface of major leaflets (mature leaf beneath the third inflorescence) | rugose | rugose |
| pubescence (mature leaf beneath the third inflorescence) | normal | normal |
| attitude | horizontal | horizontal |
| length | medium | medium |
| width | medium | medium |
| size of leaflets | medium | medium |
| intensity of green color | medium | dark |

TABLE 1-continued

Physiological and Morphological Characteristics of Tomato Hybrid SVTH2909

| CHARACTERISTIC | SVTH2909 | PINNACLE |
|---|---|---|
| glossiness | weak | weak |
| blistering | medium | medium |
| attitude of petiole of leaflet in relation to main axis | horizontal | horizontal |
| Inflorescence | | |
| type | mainly uniparous | mainly uniparous |
| type (third inflorescence) | forked | simple |
| average number of flowers in inflorescence (third inflorescence) | 4.93 | 6.47 |
| leafy or "running" inflorescence (third inflorescence) | occasional | occasional |
| Flower | | |
| color | yellow | yellow |
| calyx | normal | normal |
| calyx-lobes | shorter than corolla | approx. equaling corolla |
| corolla color | yellow | yellow |
| style pubescence | dense/present | sparse |
| anthers | all fused into tube | all fused into tube |
| fasciation (first flower of second or third inflorescence) | absent | absent |
| abscission layer | absent | present |
| length | n/a | short |
| Fruit | | |
| surface | smooth | smooth |
| base color (mature-green stage) | apple or medium green | apple or medium green |
| pattern (mature-green stage) | uniform green | uniform green |
| green shoulder | absent | absent |
| intensity of green color excluding shoulder (before maturity) | medium | medium |
| green stripes (before maturity) | absent | absent |
| size | medium | medium |
| ratio length/diameter | small | small |
| shape in longitudinal section | oblate | oblong |
| shape of blossom end | flat | flat |
| shape of stem end | flat | indented |
| shape of pistil scar | stellate | dot |
| shape of transverse/cross section (third fruit of second or third cluster) | round | round |
| ribbing at peduncle end | absent or very weak | weak |
| depression at peduncle end | medium | weak |
| size of stem/peduncle scar | medium | medium |
| size of blossom scar | medium | small |
| point of detachment of fruit at harvest (third fruit of second or third cluster) | at calyx detachment | at pedicel joint |
| length of pedicel (third fruit of second or third cluster)(mm) | n/a | 12.37 |
| length (mature) (stem axis) (mm) | 60.70 | 51.83 |
| diameter of fruit (mm) (3rd fruit of 2nd or 3rd cluster) | 70.45 | 61.21 |
| weight (mature) (g) | 191.83 | 119.30 |
| core | present | present |
| diameter of core in cross section in relation to total diameter | large | medium |
| average number of locules | 5.50 | 3.93 |
| number of locules | 4, 5 or 6 | 3 or 4 |
| color (full ripe) | red | red |
| flesh color (full-ripe) | red/crimson | red/crimson |
| locular gel color (table-ripe) | red | red |
| flesh color distribution | with lighter and darker areas in walls | with lighter and darker areas in walls |
| time of flowering | medium | medium |
| time of maturity | medium | medium |
| glossiness of skin | medium | medium |
| firmness | medium | medium |
| ripening (blossom-to-stem axis) | uniform | blossom-to-stem end |
| ripening (peripheral-to-central-radial axis) | uniformity | uniformity |
| epidermis color | yellow | yellow |
| epidermis | normal | easy-peel |
| epidermis texture | tender | tender |
| thickness of pericarp (mm) | 6.78 | 7.24 |
| thickness of pericarp | medium | medium |

TABLE 1-continued

Physiological and Morphological Characteristics of Tomato Hybrid SVTH2909

| CHARACTERISTIC | SVTH2909 | PINNACLE |
| --- | --- | --- |
| Phenology | | |
| seeding to 50% flowering (1 open on 50% of plants) (days) | 61 | 57 |
| seeding to once over harvest (days) | 117 | 116 |
| sensitivity to silvering | insensitive | sensitive |
| fruiting season | medium | medium |
| relative maturity in areas tested | medium | medium |
| Adaptation | | |
| culture | field | field |
| principle use(s) | fresh market; home garden | fresh market; home garden |
| machine harvest | not adapted | not adapted |
| regions to which adaptation has been demonstrated | California: Sacramento and Upper San Joaquin Valley | California: Sacramento and Upper San Joaquin Valley |
| Chemistry and Composition | | |
| pH | 4.40 | 4.33 |
| Titratable acidity, as % citric acid | 0.410 | 0.409 |
| Total solids (dry matter, seeds and skin removed) (percentage total content) | 6.37 | 6.25 |
| Soluble solids as °Brix | 5.81 | 5.73 |

These are typical values. Values may vary due to environment. Values that are substantially equivalent are within the scope of the invention.

TABLE 2

Physiological and Morphological Characteristics of Tomato Line FIR-A818-0160

| CHARACTERISTIC | FIR-A818-0160 | PINNACLE |
| --- | --- | --- |
| Seedling | | |
| anthocyanin in hypocotyl of 2-15 cm seedling | present | present |
| habit of 3-4 week old seedling | normal | normal |
| Mature Plant | | |
| height (cm) | 173.67 | 146.40 |
| height | long | long |
| growth type | indeterminate | indeterminate |
| form | normal | lax, open |
| canopy size (compared to others of similar type) | large | large |
| habit | semi-erect | semi-erect |
| Stem | | |
| anthocyanin coloration of upper third | absent or very weak | weak |
| length of internode | medium | medium |
| branching | profuse | intermediate |
| branching at cotyledon or first leafy node | present | absent |
| number of nodes between first inflorescence | 6.36 | 6.57 |
| number of nodes between early (first to second, second to third) inflorescences | 1.80 | 3.73 |
| number of nodes between later developing inflorescences | 2.47 | 1.93 |
| pubescence on younger stems | moderately hairy | moderately hairy |
| Leaf | | |
| type (mature leaf beneath the third inflorescence) | potato | tomato |
| type of blade | bipinnate | bipinnate |
| margins of major leaflets (mature leaf beneath the third inflorescence) | shallowly toothed or scalloped | deeply toothed or cut, sps. |
| marginal rolling or wiltiness (mature leaf beneath the third inflorescence) | moderate | absent |
| onset of leaflet rolling (mature leaf beneath the third inflorescence) | mid season | mid season |
| surface of major leaflets (mature leaf beneath the third inflorescence) | rugose | rugose |

TABLE 2-continued

Physiological and Morphological Characteristics of Tomato Line FIR-A818-0160

| CHARACTERISTIC | FIR-A818-0160 | PINNACLE |
|---|---|---|
| pubescence (mature leaf beneath the third inflorescence) | normal | normal |
| attitude | horizontal | horizontal |
| length | long | medium |
| width | broad | medium |
| size of leaflets | large | medium |
| intensity of green color | dark | dark |
| glossiness | weak | weak |
| blistering | strong | medium |
| attitude of petiole of leaflet in relation to main axis | semi-erect | horizontal |
| Inflorescence | | |
| type | mainly uniparous | mainly uniparous |
| type (third inflorescence) | simple | simple |
| average number of flowers in inflorescence (third inflorescence) | 4.33 | 5.73 |
| leafy or "running" inflorescence (third inflorescence) | frequent | absent |
| Flower | | |
| color | yellow | yellow |
| calyx | normal | normal |
| calyx-lobes | shorter than corolla | approx. equaling corolla |
| corolla color | yellow | yellow |
| style pubescence | dense/present | sparse |
| anthers | all fused into tube | all fused into tube |
| fasciation (first flower of second or third inflorescence) | absent | absent |
| abscission layer | absent | present |
| length | n/a | short |
| Fruit | | |
| surface | smooth | smooth |
| base color (mature-green stage) | apple or medium green | apple or medium green |
| pattern (mature-green stage) | uniform green | uniform green |
| green shoulder | absent | absent |
| intensity of green color excluding shoulder (before maturity) | medium | medium |
| green stripes (before maturity) | absent | absent |
| size | medium | medium |
| ratio length/diameter | small | small |
| shape in longitudinal section | circular | oblong |
| shape of blossom end | flat | flat |
| shape of stem end | flat | indented |
| shape of pistil scar | stellate | dot |
| shape of transverse/cross section (third fruit of second or third cluster) | round | round |
| ribbing at peduncle end | absent or very weak | weak |
| depression at peduncle end | weak | weak |
| size of stem/peduncle scar | small | medium |
| size of blossom scar | medium | small |
| point of detachment of fruit at harvest (third fruit of second or third cluster) | at calyx detachment | at pedicel joint |
| length of pedicel (third fruit of second or third cluster)(mm) | n/a | 12.37 |
| length (mature) (stem axis) (mm) | 59.33 | 52.43 |
| diameter of fruit (mm) (3rd fruit of 2nd or 3rd cluster) | 59.65 | 63.71 |
| weight (mature) (g) | 128.87 | 131.60 |
| core | present | present |
| diameter of core in cross section in relation to total diameter | large | medium |
| average number of locules | 4.73 | 3.20 |
| number of locules | 4, 5 or 6 | 3 or 4 |
| color (full ripe) | red | red |
| flesh color (full-ripe) | red/crimson | red/crimson |
| locular gel color (table-ripe) | red | red |
| flesh color distribution | uniform | with lighter and darker areas in walls |
| time of flowering | early | medium |
| time of maturity | medium | medium |
| glossiness of skin | medium | medium |
| firmness | medium | medium |

TABLE 2-continued

Physiological and Morphological Characteristics of Tomato Line FIR-A818-0160

| CHARACTERISTIC | FIR-A818-0160 | PINNACLE |
|---|---|---|
| ripening (blossom-to-stem axis) | uniform | blossom-to-stem end uniformity |
| ripening (peripheral-to-central-radial axis) | uniformity | uniformity |
| epidermis color | yellow | yellow |
| epidermis | normal | easy-peel |
| epidermis texture | tender | tender |
| thickness of pericarp (mm) | 6.39 | 7.80 |
| thickness of pericarp | medium | medium |
| Phenology | | |
| seeding to 50% flowering (1 open on 50% of plants) (days) | 57 | 57 |
| seeding to once over harvest (days) | 123 | 116 |
| sensitivity to silvering | insensitive | sensitive |
| fruiting season | medium | medium |
| relative maturity in areas tested | early | medium early |
| Adaptation | | |
| culture | field | field |
| principle use(s) | fresh market; home garden | fresh market; home garden |
| machine harvest | not adapted | not adapted |
| regions to which adaptation has been demonstrated | California: Sacramento and Upper San Joaquin Valley | California: Sacramento and Upper San Joaquin Valley |
| Chemistry and Composition | | |
| pH | 4.41 | 4.25 |
| Titratable acidity, as % citric acid | 0.381 | 0.450 |
| Total solids (dry matter, seeds and skin removed) (percentage total content) | 6.83 | 6.53 |
| Soluble solids as °Brix | 6.37 | 5.93 |

These are typical values. Values may vary due to environment. Values that are substantially equivalent are within the scope of the invention.

C. Breeding Tomato Plants

One aspect of the current invention concerns methods for producing seed of tomato hybrid SVTH2909 involving crossing tomato line FIR-A818-0160 and tomato line FDR-A818-0310. Alternatively, in other embodiments of the invention, tomato hybrid SVTH2909 or tomato line FIR-A818-0160 may be crossed with itself or with any second plant. Such methods can be used for propagation of tomato hybrid SVTH2909 or tomato line FIR-A818-0160 or can be used to produce plants that are derived from tomato hybrid SVTH2909 or tomato line FIR-A818-0160. Plants derived from tomato hybrid SVTH2909 or tomato line FIR-A818-0160 may be used, in certain embodiments, for the development of new tomato varieties.

The development of new varieties using one or more starting varieties is well-known in the art. In accordance with the invention, novel varieties may be created by crossing tomato hybrid SVTH2909 followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with tomato hybrid SVTH2909 or tomato line FIR-A818-0160 for the purpose of developing novel tomato lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of tomato plants developed by this invention.

Delayed fruit ripening is a trait that is especially desirable in tomato production, in that it provides a number of important benefits including an increase in fruit shelf life, the ability to transport fruit longer distances, the reduction of spoiling of fruit during transport or storage, and an increase in the flexibility of harvest time. The ability to delay harvest is especially useful for the processing industry as tomato fruits may be picked in a single harvest. A number of genes have been identified as playing a role in fruit ripening in tomato. Mutations in some of these genes were observed to be correlated with an extended shelf life phenotype (Garg et al., *Adv. Hort. Sci.* 22: 54-62, 2008). For example, WO2010042865 discloses that certain mutations in the 2nd or 3rd exon in the non-ripening (NOR) gene can result in extended shelf life phenotypes. These mutations are believed to result in an early stop codon. It is therefore expected that any mutation resulting in an early stop codon in an exon in the NOR gene, particularly a mutation resulting in an early stop codon in the 3rd exon, will result in a slower ripening or an extended shelf life phenotype in tomato. A marker to select for the unique mutation of each allele and to distinguish between the different alleles of the NOR gene in a breeding program can be developed by methods known in the art.

D. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those tomato plants which are developed by a plant breeding technique called backcrossing or by genetic engineering, wherein essentially all of the morphological and physiological characteristics of a variety are recovered or conserved in addition to the single locus introduced into the variety via the backcrossing or genetic engineering technique, respectively. By essentially all of the morphological and physiological characteristics, it is meant that the characteristics of a plant are recovered or conserved that are otherwise present when compared in the same environment, other than an occasional variant trait that might arise during backcrossing, introduction of a transgene, or application of a genetic engineering technique.

Backcrossing methods can be used with the present invention to improve or introduce a characteristic into the present variety. The parental tomato plant which contributes the locus for the desired characteristic is termed the nonrecurrent or donor parent. This terminology refers to the fact that the nonrecurrent parent is used one time in the backcross protocol and therefore does not recur. The parental tomato plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a tomato plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny tomato plants of a backcross in which a plant described herein is the recurrent parent comprise (i) the desired trait from the non-recurrent parent and (ii) all of the physiological and morphological characteristics of tomato the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.*, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming, or otherwise disadvantageous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In particular embodiments of the invention, marker assisted selection is used to increase the efficiency of a backcrossing breeding scheme for producing a tomato line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

E. Plants Derived by Genetic Engineering

Various genetic engineering technologies have been developed and may be used by those of skill in the art to introduce traits in plants. In certain aspects of the claimed invention, traits are introduced into tomato plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved tomato lines can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a tomato plant genome (see, for example Sauer et al., *Plant Physiol,* 170(4):1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well-known to those of skill in the art and applicable to many crop species include, but are not limited to, electroporation, microprojectile bombardment, *Agrobacterium*-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol.*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, for example, Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, for example, Odel et al., *Nature*, 313:810, 1985), including in monocots (see, for example, Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); the nopaline synthase promoter (An et al., *Plant Physiol.*, 88:547, 1988); the octopine synthase promoter (Fromm et al., *Plant Cell*, 1:977, 1989); the figwort mosaic virus (P-FMV) promoter as described in U.S. Pat. No. 5,378,619; an enhanced version of the FMV promoter (P-eFMV) where the promoter sequence of P-FMV is duplicated in tandem; the cauliflower mosaic virus 19S promoter; a sugarcane bacilliform virus promoter; a *commelina* yellow mottle virus promoter; and other plant virus promoters known to express in plant cells.

A variety of plant gene promoters that are regulated in response to environmental, hormonal, chemical, or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals, such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see, for example, Gibson and Shillito, *Mol. Biotech.*, 7:125, 1997). Thus, any gene which produces a protein or mRNA which expresses a phenotype or morphology change of interest is useful for the practice of the present invention.

F. Definitions

In the description and tables herein, a number of terms are used. In order to provide a clear and consistent understanding of the specification and claims, the following definitions are provided:

Allele: Any of one or more alternative forms of a genetic locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions or transgenes from one genetic background into another.

Crossing: The mating of two parent plants.

Cross-Pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence, or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) Color Chart Value: The RHS Color Chart is a standardized reference which allows accurate identification of any color. A color's designation on the chart describes its hue, brightness, and saturation. A color is precisely named by the RHS Color Chart by identifying the group name, sheet number, and letter, e.g., Yellow-Orange Group 19A or Red Group 41B.

Self-Pollination: The transfer of pollen from the anther to the stigma of the same plant.

Single Locus Converted (Conversion) Plant: Plants which are developed by a plant breeding technique called backcrossing or genetic engineering of a locus, wherein essentially all of the morphological and physiological characteristics of a tomato variety are recovered in addition to the characteristics of the single locus.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a tomato plant by transformation or site-specific modification.

G. Deposit Information

A deposit of at least 625 seeds of tomato line FIR-A818-0160 and tomato line FDR-A818-0310, disclosed above and recited in the claims, has been made with the Provasoli-Guillard National Center for Marine Algae and Microbiota (NCMA), 60 Bigelow Drive, East Boothbay, Maine, 04544 USA and the American Type Culture Collection (ATCC), 10801 University Blvd., Manassas, VA 20110-2209, respectively. The dates of deposit for those deposited seeds of tomato line FIR-A818-0160 and tomato line FDR-A818-0310 are Jun. 9, 2022 and Dec. 26, 2019, respectively. The accession numbers for those deposited seeds of tomato line FIR-A818-0160 and tomato line FDR-A818-0310 are NCMA Accession No. 202206010 and ATCC Accession No. PTA-126592, respectively. Upon issuance of a patent, all restrictions upon the deposits will be removed, and the deposits are intended to meet all of the requirements of 37 C.F.R. §§ 1.801-1.809. The deposits have been accepted under the Budapest Treaty and will be maintained in the depository for a period of 30 years, 5 years after the last request, or the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed:

1. A tomato plant comprising at least a first set of the chromosomes of tomato line FIR-A818-0160, a sample of seed of said line having been deposited under NCMA Accession No. 202206010.

2. A tomato seed that produces the plant of claim 1.

3. The plant of claim 1, wherein the plant is a plant of said tomato line FIR-A818-0160, a sample of seed of said line having been deposited under NCMA Accession No. 202206010.

4. The plant of claim 1, wherein the plant is a plant of tomato hybrid SVTH2909, and wherein said plant further comprises a set of the chromosomes of tomato line FDR-A818-0310, a sample of seed of said line having been deposited under ATCC Accession No. PTA-126592.

5. The seed of claim 2, wherein the seed is a seed of said tomato line FIR-A818-0160, a sample of seed of said line having been deposited under NCMA Accession No. 202206010.

6. A tomato seed that produces the plant of claim 4.

7. A plant part of the plant of claim 1, wherein the plant part comprises a cell of said plant.

8. A tomato plant having all of the physiological and morphological characteristics of the plant of claim 4.

9. A tissue culture of regenerable cells of the plant of claim 1.

10. A method of vegetatively propagating the plant of claim 1, the method comprising the steps of:
    (a) collecting tissue capable of being propagated from the plant of claim 1; and
    (b) propagating a tomato plant from said tissue.

11. A method of introducing a trait into a tomato line, the method comprising:
    (a) utilizing as a recurrent parent the plant of claim 3 by crossing said plant with a donor plant that comprises a trait to produce $F_1$ progeny;
    (b) selecting an $F_1$ progeny that comprises the trait;
    (c) backcrossing the selected $F_1$ progeny with a plant of the same line used as the recurrent parent in step (a) to produce backcross progeny;
    (d) selecting a backcross progeny comprising the trait and otherwise comprising the morphological and physiological characteristics of the recurrent parent line used in step (a); and
    (e) repeating steps (c) and (d) three or more times to produce a selected fourth or higher backcross progeny.

12. A tomato plant produced by the method of claim 11, wherein said plant comprises the trait and otherwise comprises all of the physiological and morphological characteristics of tomato line FIR-A818-0160.

13. A method of producing a tomato plant comprising an added trait, the method comprising introducing a transgene conferring the trait into the plant of claim 1.

14. A tomato plant produced by the method of claim 13, wherein said plant comprises the trait and otherwise comprises all of the physiological and morphological characteristics of tomato line FIR-A818-0160 or tomato hybrid SVTH2909.

15. A tomato plant comprising at least a first set of the chromosomes of tomato line FIR-A818-0160, a sample of seed of said line having been deposited under NCMA Accession No. 202206010, further comprising a transgene.

16. The plant of claim 15, wherein the transgene confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

17. A tomato plant comprising at least a first set of the chromosomes of tomato line FIR-A818-0160, a sample of seed of said line having been deposited under NCMA Accession No. 202206010, further comprising a single locus conversion.

18. The plant of claim 17, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

19. A method for producing a seed of a tomato plant, the method comprising the steps of:
    (a) crossing the plant of claim 1 with itself or a different tomato plant; and
    (b) allowing a seed of a derived tomato plant to form.

20. A method of producing a seed of a derived tomato plant, the method comprising the steps of:
    (a) producing a derived tomato plant from a seed produced by crossing the plant of claim 1 with itself or a different tomato plant; and
    (b) crossing the derived tomato plant with itself or a different tomato plant to obtain a seed of a further derived tomato plant.

21. The method of claim 20, the method further comprising repeating said producing and crossing steps of (a) and (b) using the seed from said step (b) for at least one generation to produce a seed of an additional derived tomato plant.

22. A method of producing a tomato fruit, the method comprising:
    (a) obtaining the plant of claim 1, wherein the plant has been cultivated to maturity; and
    (b) collecting a tomato fruit from the plant.

23. The tomato plant of claim 1, wherein the plant is a hybrid tomato plant.

24. A tomato seed that produces the plant of claim 23.

* * * * *